United States Patent [19]

Sakurai

[11] 4,273,125
[45] Jun. 16, 1981

[54] TAMPON

[75] Inventor: Akira Sakurai, Utsunomiya, Japan

[73] Assignee: Kao Soap Co., Ltd., Tokyo, Japan

[21] Appl. No.: 132,249

[22] Filed: Mar. 20, 1980

[30] Foreign Application Priority Data

Apr. 12, 1979 [JP] Japan .................................. 54-44582

[51] Int. Cl.³ .............................................. A61F 15/00
[52] U.S. Cl. .................................................. 128/263
[58] Field of Search ......................... 128/263, 270, 285

[56] References Cited

U.S. PATENT DOCUMENTS

| 2,829,646 | 4/1958 | Kurkjian | 128/263 |
| 3,034,508 | 5/1962 | Nalle, Jr. | 128/263 |
| 3,090,385 | 5/1963 | Brecht | 128/263 |
| 3,830,236 | 8/1974 | Hanke | 128/263 |

FOREIGN PATENT DOCUMENTS 700840 12/1964 Canada ..................................... 128/263

Primary Examiner—C. Fred Rosenbaum
Attorney, Agent, or Firm—Blanchard, Flynn, Thiel, Boutell & Tanis

[57] ABSTRACT

An applicator-type tampon in which a mass of absorbent material is contained in an outer cylinder and a pusher structure has pusher members movable through one or more openings in the side wall of the outer cylinder for displacing the mass of absorbent material from the outer cylinder into the vagina.

7 Claims, 16 Drawing Figures

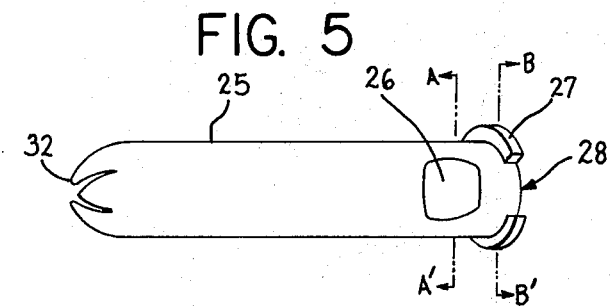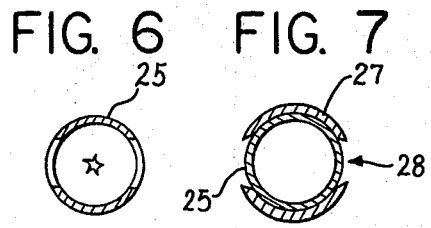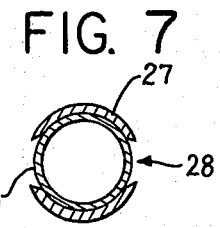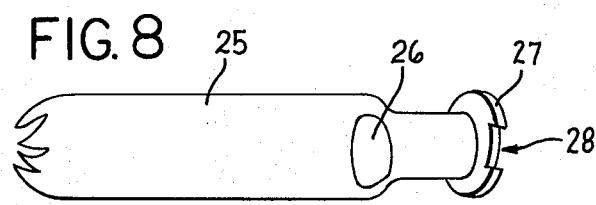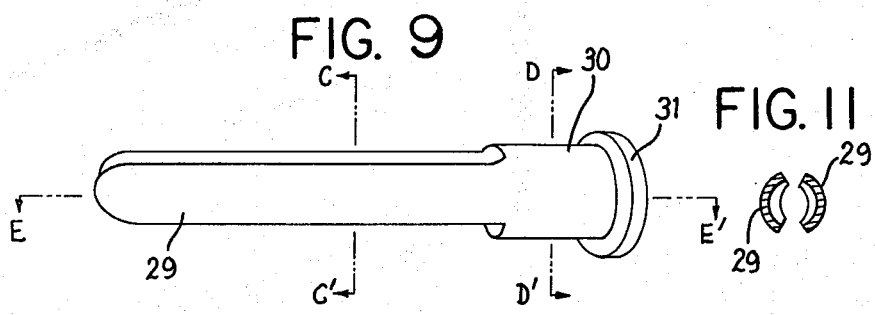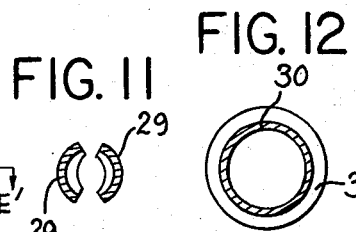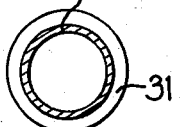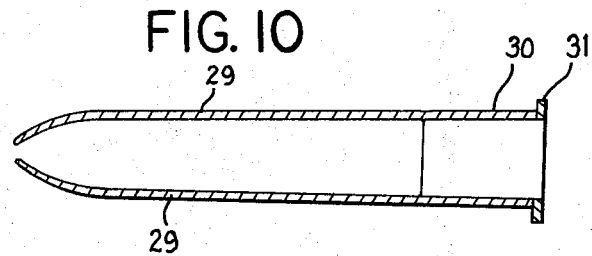

TAMPON

The present invention relates to a hygienic, applicator-type tampon. More particularly, the present invention relates to an applicator-type tampon having push-out pieces which are held in contact with the outer face of an outer cylinder before the tampon is used and which are extended into the interior of the outer cylinder through holes formed in the outer cylinder to provide a push-out portion when the tampon is to be used.

In the past, most hygienic catamenial articles were of the napkin type, but recently the demand for hygienic catamenial articles of the tampon type has been increasing. Hygienic catamenial articles of the tampon type may be divided into the following general types according to the construction thereof.

(1) Finger Type

Typically, there is used an absorbing member formed by compression molding of an absorbing material, such as absorbent cotton or rayon. When a tampon of this type is used, the wrapping cover is completely removed and the tampon is inserted into the body by the user's fingers. The great advantage of a tampon of this type is that the size of the hygienic catamenial article is diminished. The size of a tampon of this type is much smaller than the size of a sanitary napkin and a tampon of this type can be conveniently carried in a handbag or the like. However, since the absorbing member to be inserted is directly touched by the user's fingers and it is inserted by the user's fingers, which inevitably contact unsanitary areas located before the insertion location, a tampon of this type is insufficient from the sanitary viewpoint.

(2) Stick Type

The absorbing member used is similar to the absorbing member used for the above-mentioned tampon of the type (1). An appropriate hole is formed in the tail portion of the absorbing member and one end of a stick-like application tool formed from a material such as paper is placed in this hole. The application tool is gripped by the user's fingers and the absorbing member is thereby introduced into the body. From the sanitary viewpoint, a tampon of this type is improved in comparison with a tampon of the type (1). However, since the absorbing member is inserted by using a stick which is much smaller than the absorbing member, the insertion operation is very unstable and the user cannot but have an uneasy feeling.

(3) Applicator Type

There is used an inserting tool comprising inner and outer cylinders which are slidable relative to each other. The inner and outer cylinders are formed from paper or plastic material. The absorbing member is contained in the interior of the outer cylinder and it is pushed out by sliding the inner cylinder inwardly from the opening on the outer end of the outer cylinder and the absorbing member is thereby inserted into the body. The sanitary problem encountered with the tampon of the type (1) is solved substantially completely. However, a tampon of this type involves the following disadvantages: (1) falling-out of the inner cylinder from the outer cylinder readily occurs because an appropriate fit is not attained between the inner and outer cylinders and (2) because the above-mentioned inserting tool is used, the length of the tampon as a whole is more than 2 times longer than the length of the absorbing member and the tampon is not convenient to carry out.

The tampon according to the present invention belongs to the above-mentioned applicator-type (3). The present invention relates to an improvement in a hygienic tampon of the applicator type, which has an improved mechanism for inserting the absorbing member by using an insertion tool. The invention provides an applicator-type tampon in which the abovementioned defects are eliminated.

Various applicator-type tampons have heretofore been proposed, and typical examples will now be described with reference to FIGS. 1 to 4 of the accompanying drawings.

BRIEF DESCRIPTION OF THE DRAWINGS

FIG. 5 is a perspective view showing one embodiment of the outer cylinder of the applicator of the present invention.

FIG. 6 is a sectional view taken along the line A-A' in FIG. 5.

FIG. 7 is a sectional view taken along the line B-B' in FIG. 5.

FIG. 8 is a perspective view showing another embodiment of the outer cylinder of the applicator of the present invention.

FIG. 9 is a perspective view showing one embodiment of the push-out portion of the applicator of the present invention.

FIG. 10 is a sectional view taken along the line E-E' in FIG. 9.

FIG. 11 is a sectional view taken along the line C-C' in FIG. 9.

FIG. 12 is a sectional view taken along the line D-D' in FIG. 9.

Figure 1:
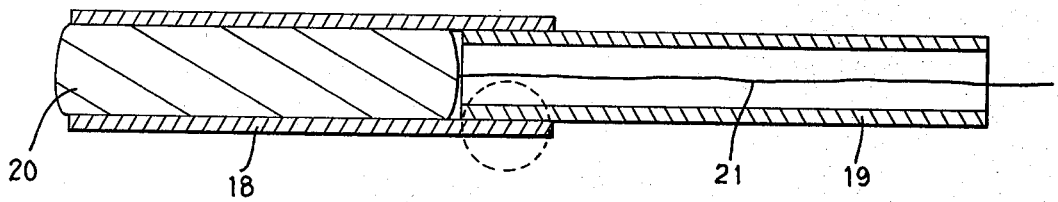
FIG. 1 is a longitudinal sectional view of a prior art tampon including an applicator formed of paper.
Figure 2:
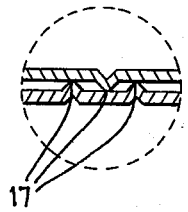
FIG. 2 is an enlarged view of the portion within the broken line circle of FIG. 1 and showing the cylinder-connecting portion of the tampon.

The prior art tampon shown in FIG. 1, including an applicator formed of paper, has already been marketed. In this tampon, the outer and inner cylinders 18 and 19 are arranged as illustrated in FIG. 1, and an absorbing member 20 is contained in the outer cylinder 18. A removal string 21 extends to the outside through the interior of the inner cylinder 19. When the tampon is actually used, the outer cylinder 18 is inserted into the body and the inner cylinder 19 is then slid toward the interior of the body, and the absorbing member 20 is thereby pushed out into the body and insertion is thus completed. In the tampon of this type, as shown in an enlarged scale in FIG. 2, in order to prevent falling-out of the inner cylinder 19, projections 17 are formed by pressing the outer and inner cylinders. However, falling-out of the inner cylinder cannot be completely prevented by such projections. Furthermore, the length of the applicator is more than 2 times the length of the absorbing member and the tampon has the disadvantage that it cannot be conveniently carried about.

Figure 3:
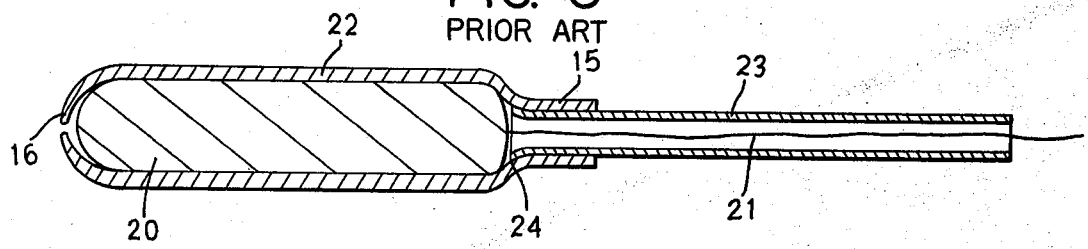
FIG. 3 is a longitudinal sectional view of another prior art tampon including an applicator formed of a plastic material.

A tampon comprising an applicator formed of a plastic material, as shown in FIG. 3, has been marketed subsequently to the above tampon of FIG. 1, including an applicator formed of paper.

Figure 4:
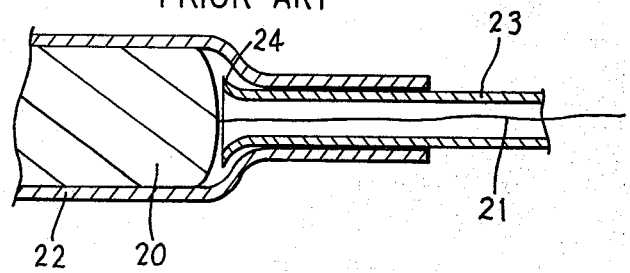
FIG. 4 is an enlarged view showing the cylinder-connecting portion of the tampon of FIG. 3.

The tampon shown in FIG. 3 comprises an outer cylinder 22 having a semi-spherical end portion 16 on the inner or insertion (leftward) end thereof. The end portion 16 has slits extending radially from the apex thereof to form triangular lips that can be flexed outwardly. The absorbing member 20 is contained within the outer cylinder 22. The outer cylinder 22 has a tail portion 15 having a diameter slightly smaller than the diameter of the outer cylinder proper. An inner cylinder 23 has an enlarged inner end 24 disposed inside the outer cylinder 22 so that it cannot fall out of the cylinder (FIG. 4). When the tampon is used, the inner cylinder 23 is slid axially in the outer cylinder 22, as in the case of the tampon shown in FIG. 1, and the absorbing member 20 is thereby inserted into the body.

In the tampon shown in FIG. 3, because of the rounding of the insertion (leftward) end of the outer cylinder, the feel at the time of insertion is improved. Also, falling out of the inner cylinder is more effectively prevented. However, the disadvantage that the tampon has an undesirably great length is not eliminated.

We conducted research with a view to developing an applicator-type tampon in which the foregoing disadvantages are eliminated, and we have now completed the present invention.

It is, therefore, a primary object of the present invention to provide an applicator-type tampon which is characterized in that (i) the tampon is excellent from the sanitary viewpoint, (ii) falling out of the inner cylinder from the outer cylinder is prevented while the tampon is carried about, (iii) the length is small and (iv) an unpleasant feeling is not given when the tampon is actually inserted.

More specifically, in accordance with the present invention, there is provided an improvement in a tampon comprising an applicator of the type including an outer cylinder and a push-out portion which is slidably movable from the outer end of the outer cylinder to the inner or insertion end of the outer cylinder for inserting into the body and an absorbing member contained in said outer cylinder. According to the invention, the outer cylinder has one or more holes which are located at a distance from the insertion end of the applicator, which distance is longer than the length of the absorbing member. The applicator comprises a second cylinder having one or more push-out pieces projecting lengthwise thereof. The push-out pieces have a width slightly smaller than the width of the holes in the outer cylinder in the circumferential direction of the outer cylinder. The number of said push-out pieces is the same as the number of the holes formed in the outer cylinder. The applicator is arranged so that before the tampon is to be used, the push-out pieces are maintained in contact with the outer surface of the outer cylinder and when the tampon is to be inserted, the push-out pieces are extended through the holes of the outer cylinder into the interior thereof so that the absorbing member contained in the outer cylinder can be pushed out by sliding the push-out pieces axially inside the outer cylinder.

In the tampon of the present invention, because the push-out pieces are fitted on the outer cylinder and are maintained in contact with the outer surface of the outer cylinder before the tampon is inserted into the body, the length of the applicator is only slightly longer than the length of the absorbing member and the length of the tampon as a whole is much shorter than the lengths of the conventional applicator-type tampons. When the tampon is to be inserted, the push-out pieces are slid rearwardly until the inner ends of the push-out pieces arrive at the holes in the outer cylinder and then the push-out pieces are automatically guided into the holes because of the curvature and flexibility of the inner ends of the push-out pieces. When the push-out pieces are then slid forwardly, the absorbing member is pushed out forwardly from the outer cylinder in the insertion direction. Accordingly, the insertion operation is remarkably facilitated.

Preferred embodiments of the tampon of the present invention will now be described with reference to FIGS. 5 to 16 of the accompanying drawings.

As shown in FIGS. 5 through 8, the outer cylinder 25 has one or more through holes 26 formed therein at a location spaced from the insertion (leftward) end 32 of the outer cylinder a distance longer than the length of the absorbing member contained in the outer cylinder. Notches 28 are formed in an annular supporting piece 27 mounted in or formed on the outer (rightward) end of the outer cylinder 25 at positions in longitudinal alignment with the positions of the holes 26. As shown in FIG. 7, it is preferred that the width of the notches 28 is substantially equal to the width of the push-out pieces 29 in the vicinity of the radially inner side of the annular supporting piece 27, but that the width of the notches 28 is smaller than that of the push-out pieces 29 in the radially outer side of the annular supporting piece 27, so that after the push-out pieces 29 have been fitted in the notches 28, they are not easily separated therefrom in a radial direction. In other words, the notches 28 are undercut to some extent. With this arrangement is employed, when the push-out portion 30 is drawn out outwardly (rightwardly), separation of the push-out pieces 29 from the outer cylinder 25 can be effectively prevented. Furthermore, it is preferred that the inner (leftward) end 32 of the outer cylinder 25 be constructed by a plurality of split pieces (spherical triangles) forming a substantially semi-spherical surface. The bases of the spherical triangles are integral with the outer cylinder 25 so that they can flex outwardly. If the inner (leftward) end 32 of the outer cylinder 25 is thus constructed, the resistance to insertion of the outer cylinder 25 into the vagina is reduced. Moreover, it is preferred that, as shown in FIG. 8, the outer diameter of the outer cylinder 25 outwardly (rightwardly) from the holes 26 be smaller than the outer diameter of the outer cylinder 25 inwardly (leftwardly) of the holes 26, because the flexural stress of the push-out pieces 29 on the notches 28 is thereby moderated.

As shown in FIGS. 9 through 12, the push-out portion of the applicator includes a cylinder 30 having push-out pieces 29 projecting axially inwardly (leftwardly) therefrom. The push-out pieces 29 have a width slightly smaller than the dimension of the holes 26 in the outer cylinder 25 in the circumferential direction, the number of said push-out pieces 29 being the same as the number of the holes 26. A push-out portion-supporting piece 31 is provided on the outer (rightward) end of the cylinder 30. It is preferred that these members be integrally formed and that the inner (leftward) ends of the push-out pieces 29 be inwardly curved so that they snugly contact the semi-spherical end 32 of the outer cylinder 25.

Figure 13:
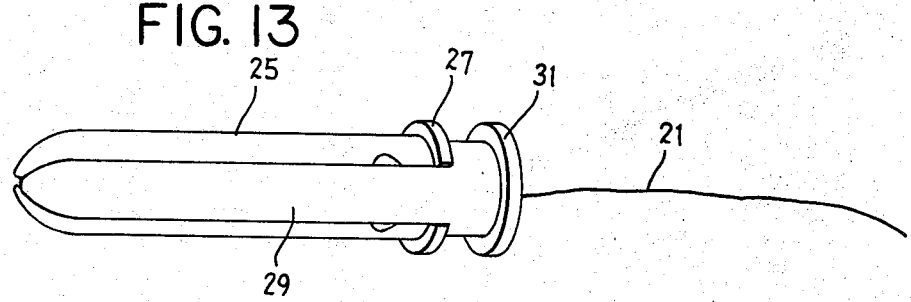
FIG. 13 is a perspective view showing the tampon of the present invention before application.

Before the tampon of the present invention is used, as shown in FIG. 13, the push-out portion is fitted in and is fixed to the outer cylinder 25 so that the push-out pieces 29 are maintained in contact with the outer surface of the outer cylinder, and the absorbing member is contained inside the outer cylinder.

Figure 14:
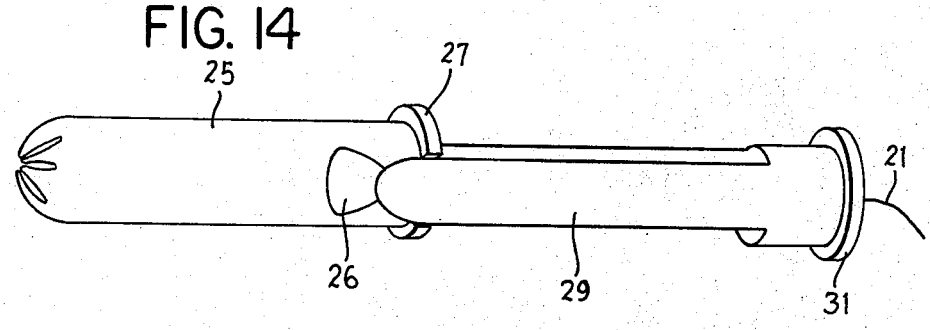
FIG. 14 is a perspective view showing the tampon of the present invention just before insertion.
Figure 15:
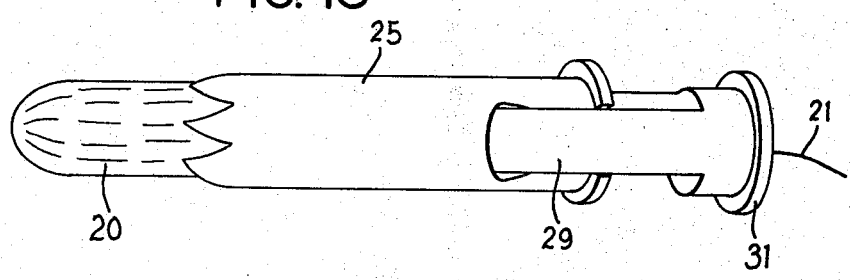
FIG. 15 is a perspective view showing the tampon of the present invention at the time of insertion.
Figure 16:
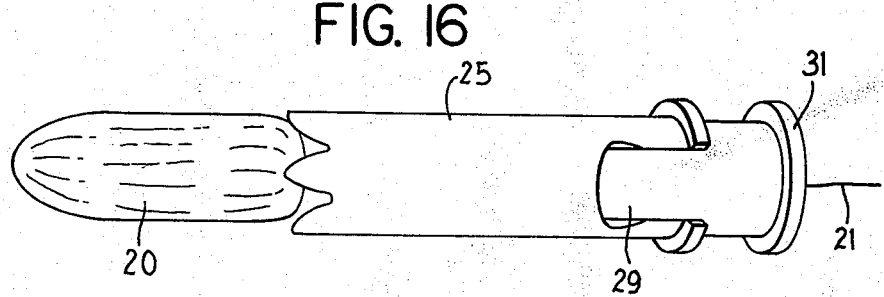
FIG. 16 is a perspective view showing the tampon of the present invention in the state where insertion is completed.

When the tampon of the present invention is to be inserted, as shown in FIG. 14, the push-out portion-supporting piece 31 is slid outwardly (rightwardly) while the annular supporting piece 27 is held fixed. The push-out pieces 29 are thereby slid outwardly along the outer side of the outer cylinder 25. When the inner (leftward) ends of the push-out pieces 29 arrive at the holes 26, because the inner ends of the push-out pieces 29 are radially inwardly curved, they are guided into the holes 26 and extend into the interior of the outer cylinder 25. In this state, the outer cylinder 25 is inserted into the vagina, and the push-out portion-supporting piece 31 is slid inwardly (leftwardly) as shown in FIG. 15. At this point, the tail portion of the absorbing member 20 is pushed out by the inner (leftward) ends of the push-out pieces 29 and is transferred into the body through the inner opening portion of the outer cylinder 25, and the absorbing member 20 is completely pushed out from the outer cylinder 25 as shown in FIG. 16. Thus, insertion is completed.

The applicator that is used for the tampon of the present invention can be formed of plastic, paper and other appropriate materials by molding, in the same manner as the conventional applicators. The material of which the applicator is made is not critical in the present invention.

In preparing tampons, according to the conventional techniques, the absorbing member can be inserted into the outer cylinder only before the inner cylinder is inserted as is seen from FIG. 3. According to the present invention, the absorbing member can be packed before or after the push-out portion is assembled, that is, it can be inserted through the open outer (rightward) end of outer cylinder 25 or through the open outer (rightward) end of cylinder 30.

The tampon of the present invention having the above-mentioned structure is excellent from the sanitary viewpoint before application. In the tampon of the present invention, troubles caused by an insufficient joining of the outer cylinder to the push-out portion do not occur. Also the length is reduced to about ½ of the length of the conventional tampons of the applicator type. Accordingly, the tampon of the present invention can be carried about very conveniently. Furthermore, by a simple operation of sliding outwardly (rightwardly) the push-out portion, the parts readily attain the state where easy insertion of the absorbent member into the body is possible. Accordingly, the tampon of the present invention affords great convenience to the user.

The embodiments of the invention in which an exclusive property or privilege is claimed are defined as follows:

1. A tampon, comprising:
an elongated outer cylinder having an outer end and having an inner end adapted for insertion into a vagina, a mass of absorbent material disposed inside said outer cylinder close to the inner end thereof and adapted to be moved through said inner end of said outer cylinder, said outer cylinder having one or more through holes formed in the side wall thereof at a location spaced from the inner end of said outer cylinder and in the region of the outer end of said mass of absorbent material;
a push-out member mounted on said outer cylinder for sliding movement in a direction lengthwise thereof, said push-out member having one or more longitudinally extending push-out pieces corresponding in number to the number of said holes, said push-out pieces being disposed outside of said outer cylinder, said push-out pieces having a size such that they can be extended through said holes into the interior of said outer cylinder for engaging said mass of absorbent material in response to movement of said push-out member relative to said outer cylinder and then longitudinal movement of said push-out member in a direction toward the inner end of said outer cylinder causes said push-out pieces to move said mass of absorbent material out of said outer cylinder through the inner end thereof.

2. A tampon as claimed in claim 1, in which said through hole or holes is or are spaced from the inner end of said outer cylinder a distance larger than the length of said mass of absorbent material, said push-out member being located adjacent the outer end of said outer cylinder with said push-out pieces extending longitudinally therefrom and slidably engaging the outer surface of the side wall of said outer cylinder.

3. A tampon as claimed in claim 2 wherein the inner end of said outer cylinder has a semi-spherical face having slits therein defining flexible flaps so that said mass of absorbent material can be moved therethrough, said push-out pieces extending substantially to said face and the end portions of said push-out pieces being inwardly curved to engage portions of said semi-spherical face.

4. A tampon as claimed in claim 1, claim 2 or claim 3, wherein the portion of said outer cylinder between said holes and the outer end thereof is of smaller diameter than the portion of said outer cylinder between said holes and the inner end thereof.

5. A tampon as claimed in claim 1, claim 2 or claim 3 in which said push-out member comprises a second cylinder coaxial with said outer cylinder, said push-out pieces extending longitudinally from one axial end of said second cylinder.

6. A tampon as claimed in claim 1, claim 2 or claim 3 in which said outer cylinder has laterally outwardly extending guide wall means for engaging the longitudinal edges of said push-out pieces for guiding longitudinal movement thereof.

7. A tampon as claimed in claim 1, claim 2 or claim 3 in which said outer cylinder has two holes located on diametrically opposite portions thereof and has a laterally outwardly extending annular flange on the outer end thereof, said flange having two slots therethrough in longitudinal alignment with said holes, said push-out member comprises a second cylinder coaxial with and of substantially the same diameter as said outer cylinder and being disposed outwardly from said outer end of said outer cylinder, said push-out pieces comprising two elongated, diametrically opposed legs extending longitudinally from said second cylinder, through said slots and lengthwise of said outer cylinder substantially to the inner end thereof, said legs being curved to conform to the circumferential curvature of the opposing portions of the external surface of said outer cylinder that they slidably engage.

* * * * *